United States Patent
Sørensen (10) Patent No.: US 9,900,687 B2
(45) Date of Patent: Feb. 20, 2018

(54) EARPHONE DEVICE WITH OPTICAL SENSOR

(71) Applicant: GN Netcom A/S, Ballerup (DK)

(72) Inventor: Michael Sørensen, Jyllinge (DK)

(73) Assignee: GN NETCOM A/S (DK)

( * ) Notice: Subject to any disclaimer, the term of this patent is extended or adjusted under 35 U.S.C. 154(b) by 0 days.

(21) Appl. No.: 15/027,595

(22) PCT Filed: Oct. 7, 2013

(86) PCT No.: PCT/EP2013/070829
§ 371 (c)(1),
(2) Date: Apr. 6, 2016

(87) PCT Pub. No.: WO2015/051819
PCT Pub. Date: Apr. 16, 2015

(65) Prior Publication Data
US 2016/0249133 A1  Aug. 25, 2016

(51) Int. Cl.
*H04R 3/00* (2006.01)
*H04R 1/10* (2006.01)
(Continued)

(52) U.S. Cl.
CPC .......... *H04R 3/00* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS

2007/0189570 A1* 8/2007 Matsuo ............... H04R 1/1016
381/382
2009/0281435 A1 11/2009 Ahmed et al.
(Continued)

FOREIGN PATENT DOCUMENTS

JP    2008136556      6/2008
WO   WO 2009/001449  12/2008
WO   WO 2012/103273   8/2012

OTHER PUBLICATIONS

Atsushi et al, english translation of WO2009001449. pp. 1-15. Dec. 31, 2008.*

(Continued)

*Primary Examiner* — Curtis Kuntz
*Assistant Examiner* — Qin Zhu
(74) *Attorney, Agent, or Firm* — Altera Law Group, LLC (57) ABSTRACT

An earphone device (1) to be worn in the ear, which earphone device (1) comprising a main body (18) to be arranged in the concha (19) of the outer ear (14) of a user and an optical sensor (35), which optical sensor (35) comprises a light emitter (16) and a light detector (17). The earphone device (1) comprises window means (8, 9) through which light emitted by the light emitter (16) can be transmitted. The window means (8, 9) comprises an end face (31) adapted to abut a conchal wall (37) at a sensing position (36). The main body (18) comprises a speaker protrusion (26) to be inserted into to ear canal (15). The distance between the speaker protrusion (26) and the end face (31) is adjustable.

11 Claims, 7 Drawing Sheets

(51) Int. Cl.
*H04R 1/08* (2006.01)
*A61B 5/00* (2006.01)
*A61B 5/024* (2006.01)
*A61B 5/11* (2006.01)

(52) U.S. Cl.
CPC .......... *A61B 5/6803* (2013.01); *A61B 5/6817* (2013.01); *A61B 5/6898* (2013.01); *H04R 1/08* (2013.01); *H04R 1/105* (2013.01); *H04R 1/1016* (2013.01); *H04R 1/1033* (2013.01); *H04R 1/1041* (2013.01); *H04R 1/1058* (2013.01); *H04R 1/1066* (2013.01); *A61B 5/11* (2013.01); *A61B 5/721* (2013.01); *H04R 2420/07* (2013.01); *H04R 2420/09* (2013.01)

(56) References Cited

U.S. PATENT DOCUMENTS

| | | | | |
|---|---|---|---|---|
| 2010/0217098 | A1* | 8/2010 | LeBoeuf | A61B 5/00 600/301 |
| 2010/0217103 | A1* | 8/2010 | Abdul-Hafiz | A61B 5/14552 600/322 |
| 2012/0197093 | A1 | 8/2012 | Leboeuf et al. | |
| 2013/0131519 | A1 | 5/2013 | Leboeuf et al. | |
| 2013/0336495 | A1* | 12/2013 | Burgett | H04R 1/1091 381/74 |

OTHER PUBLICATIONS

International Search Report for PCT/EP2013/070829 dated Apr. 8, 2014.

* cited by examiner

Figure 15

EARPHONE DEVICE WITH OPTICAL SENSOR

TECHNICAL FIELD

The invention relates to an earphone device to be worn in the ear, which earphone device comprising a main body to be arranged in the concha of the outer ear of a user, which main body comprises a speaker protrusion to be inserted into to ear canal, and an optical sensor, which optical sensor comprises a light emitter and a light detector, and wherein the earphone device comprises window means through which light emitted by the light emitter can be transmitted, which window means comprises an end face adapted to abut a conchal wall at a sensing position.

BACKGROUND ART

Earphones or headsets with in the ear-earphones are often used to listen to music, when the user is moving around or exercising. People exercising are often also using heart rate monitors worn around the chest and connected wirelessly or by wire to a running watch or smart phone. Recently, earphones with built-in heart rate monitors are put on the market.

Heart rate can be measured at the ear by using optical plethysmography. With this technique, instantaneous changes in the volume of the blood in the tissue are detected. The detection is obtained by emitting light to the tissue of the ear and measuring changes in reflectance resulting from changes in the volume of blood in the tissue.

WO 2012/103273 (Valencell, Inc.) discloses an earbud with sensing means based on optical plethysmography.

IRiver ON™ is a headphone comprising a pair of earphones, wherein one of the earphones comprises an optical heart rate sensor. The heart rate sensor comprises a light emitter and a light detector. The light is transmitted through a first window in the earphone to the skin of the concha. Some of the light is absorbed by the skin and the underlying tissue. However, some of the light is scattered back by the vascular system of veins and arteries. Some of this light is returned through a second window immediately beside the first window to a light detector. The signal from light detector is processed and the heart rate from the user wearing the earphone can be determined. The signal from the heart rate sensor is processed with information from a motion sensor also arranged in the earphone device in order to subtract signal noise due to the movements caused by the exercising.

In order to obtain a reliable signal, it is important that the first and second sensor windows are positioned precisely in relation to the skin so that false light, which means light from the surroundings, do not reach the heart rate sensor. The first and second windows are arranged on the face of a sensor protrusion extending from earphone device and touching the conchal wall at the antitragus of the ear. The edges of the windows must abut the skin in order to not letting ambient light enter, whereby light scattered from the blood vessels cannot be detected sufficiently.

The IRiver ON™ headphone comprises an earphone device according to the preamble. This headphone comprises a neckband with electronics.

DISCLOSURE OF INVENTION

The object of the invention is to provide an earphone device according to the preamble with a possibility to adapt it to ears of different sizes in a simple and realiable way.

The earphone device according to the preamble is characterized in that the main body comprises a speaker protrusion to be inserted into to ear canal, and in that the distance between the speaker protrusion and the end face is adjustable. Thus, it is possible to obtain a good fit and a reliable sensing at the lower end of the concha although the earbud is inserted in the ear canal. As the earphone device has a speaker protrusion to be inserted in the ear canal, only a speaker of small diameter is need, whereby there is space left in the earphone device for other electronics. This means again, that a separate housing for electronics can be omitted. It is possible to keep all the necessary electronic hardware, inclusive the DSP hardware needed to subtract the "noise" from the pure heart rate signal, in the first and second earphone devices.

According to an embodiment, the optical sensor is a heart rate sensor. A very reliable heart rate sensing can be obtained by this embodiment.

According to an embodiment, the earphone device comprises a fitting member adapted to be detachably attached to the outer side of the main body, and wherein the fitting member comprises the window means. In order to adjust the distance between the speaker protrusion and the end face, the user may simply replace the fitting member with other dimensions. Thus, an earphone device may be delivered may for example 3 or 5 different replaceable fitting members.

The fitting member is preferably of resilient material, whereby detachment and attachment is easier and the user comfort is increased.

Preferably, the end face is provided at the end of a protruding sensor protrusion with a certain length.

According to an embodiment, the fitting member comprises a first window for transmitting light emitted from the light emitter to the skin of the ear and a second window for transmitting light from the skin of the ear to the light detector.

The first window and second window are preferably divided by a wall of material, which is non-transparent for the light emitted by the light emitter.

According to an embodiment, the resilient fitting member comprises a protruding conchal wall stabilizer adapted to engage the conchal wall at a second position at the crux of helix. Hereby a more comfortable fit may be obtained.

According to an embodiment, the earphone may comprise a number of replaceable fitting members of different sizes, whereby the distance between the speaker protrusion and the end face can be adjusted by replacing one of the fitting members with another fitting member.

According to another embodiment, the end face is provided at the end of an adjustable end face member.

According to a further embodiment, the optical sensor is provided at the end of an adjustable sensor member.

According to an embodiment, the earphone device is adapted to be positioned in the outer ear, so that the end face is abutting the conchal wall in the lower end of the concha at the antitragus.

According to a preferred embodiment, the earphone device comprises a resilient eargel or earbud detachably attached to the speaker protrusion. Such an earbud may, when inserted, seal the ear canal from the surroundings and improve the audio experience although the speaker is small.

The main body and the speaker protrusion may be embodied as a unitary non-resilient body.

This disclosure also relates to a headphone comprising an earphone and a number of replaceable fitting members with sensor protrusions of different lengths.

BRIEF DESCRIPTION OF THE DRAWINGS

The invention is explained in detail below with reference to the drawing illustrating a preferred embodiment of the invention and in which.

MODES FOR CARRYING OUT THE INVENTION

Figure 1:
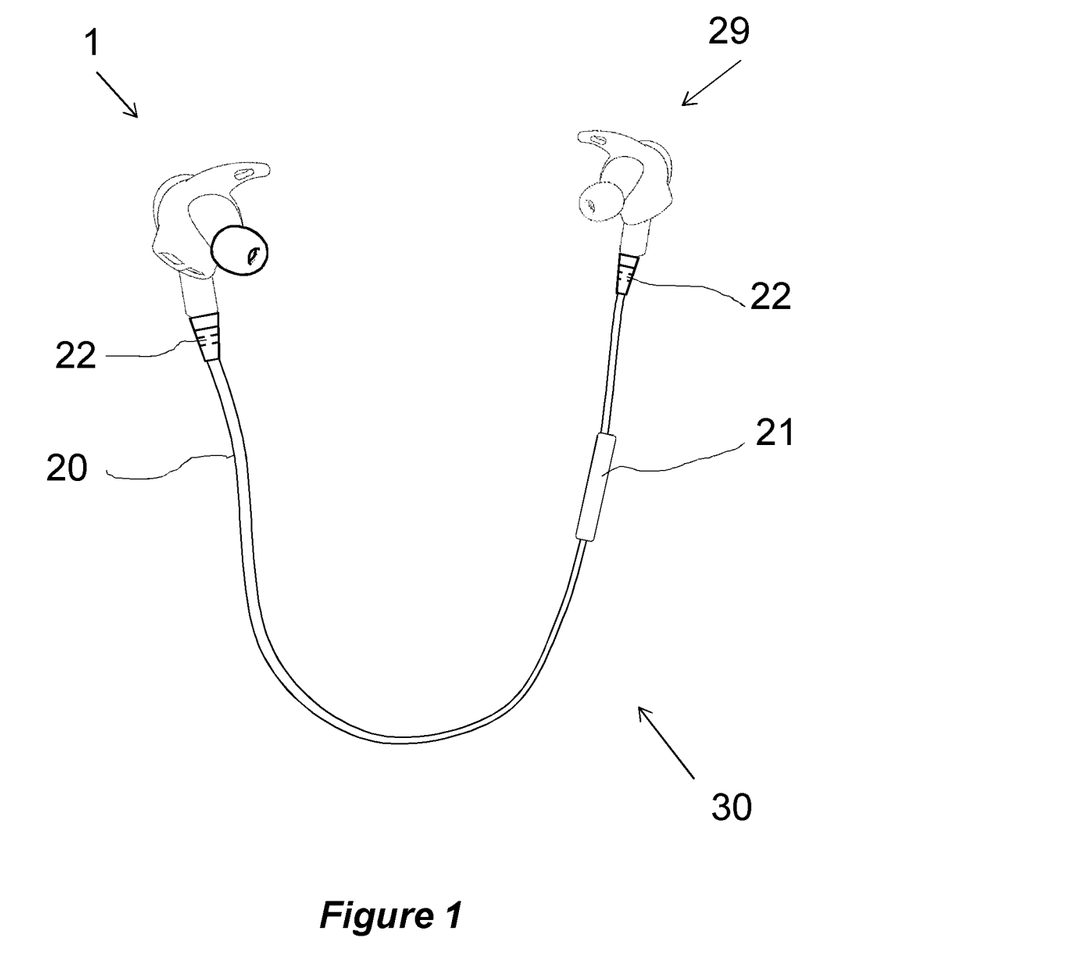
FIG. 1 is a perspective view of a preferred embodiment of headset comprising an earphone device according to the invention.

FIG. 1 is a perspective view of a preferred embodiment of a headset 30. The headset 30 is a wireless headset comprising an earphone device 1 according to the invention, a second earphone, a cord 20 interconnecting the two earphones devices 1, 29 and a controller 21 on the cord 20. The first earphone device 1 and the second earphone device 29 are of the in-the-ear type and have the same form factor. Each of them comprises a speaker. The headset is a Bluetooth® headset, whereby it can communicate wirelessly with for example a Bluetooth-enabled smartphone. The controller 21 comprises buttons for adjusting the volume, and a microphone, which is used to capture the users' voice, when the headset is used for two-way communication. The earphone devices 1, 29 also comprise relevant electronics such as battery, Bluetooth transceiver, digital signal processing circuitry, memory, antenna etc. The headset 30 is suited for use during exercising, such as running, bicycling etc. During use, the cord can be arranged behind the neck of the user.

Figure 2:
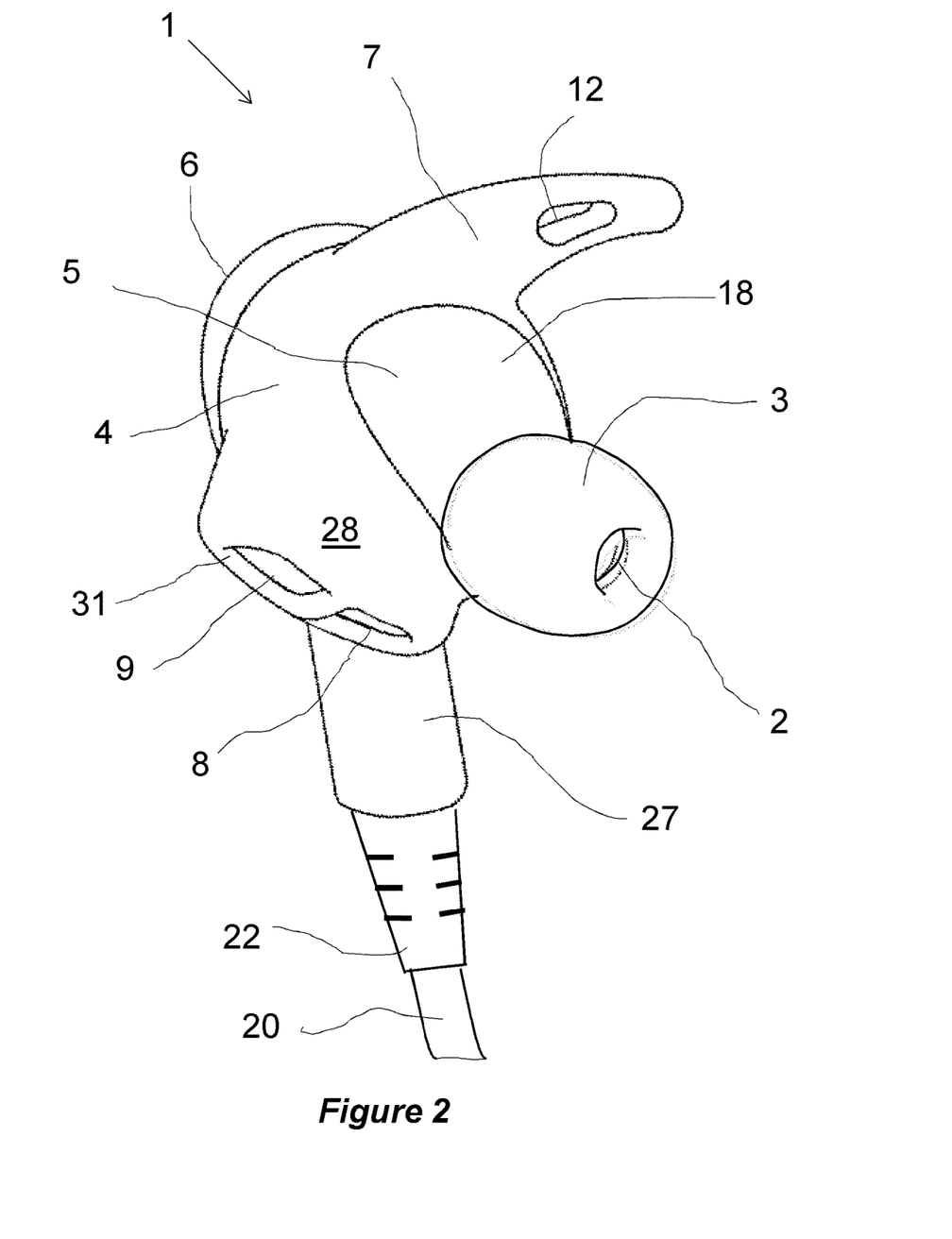
FIG. 2 is an enlarged view of an earphone device according to the invention.

FIG. 2 is an enlarged view of an earphone device 1 according to the invention. The earphone device 1 is adapted to be arranged in the right ear of the user. The earphone device 1 comprises a main body 18 with a first side 5 facing the concha when worn and a second side 6 facing away from the concha when worn. An eargel 3 with an audio opening 2 of soft material such as rubber or silicone is arranged on a speaker protrusion 26 (see FIG. 9). The eargel 3 is detachable and can be replaced with another eargel with different size in order to adapt the earphone device 1 to the size of the user's ear. The eargel 3 is adapted to be sealing arranged in the ear canal, whereby audio with high volume despite a relatively small speaker unit, can be directed to the eardrum. The main body 18 is more or less ball shaped with an elongated part 27 inclined downwards when worn. A strain relief 22 extends from the free end of the elongated part 27, and the cord 20 extends from the strain relief 22.

A more or less ring-shaped fitting member 4 of resilient material is arranged around the main body 18. The fitting member 2 comprises a conchal wall stabilizer 7 to be arranged at the upper end of the concha at the crux of helix, where it abuts the conchal wall and stabilizes the earphone device 1. A hole 12 in the conchal wall stabilizer 7 is provided to adapt the resiliency. At the opposite side, the fitting member 4 comprises a sensor protrusion 28, which extends away from the main body 18. A free end face 31 of the sensor protrusion 28 comprises first window 8 and a second window 9 and abuts the conchal wall at the antitragus area when worn.

Figure 3:
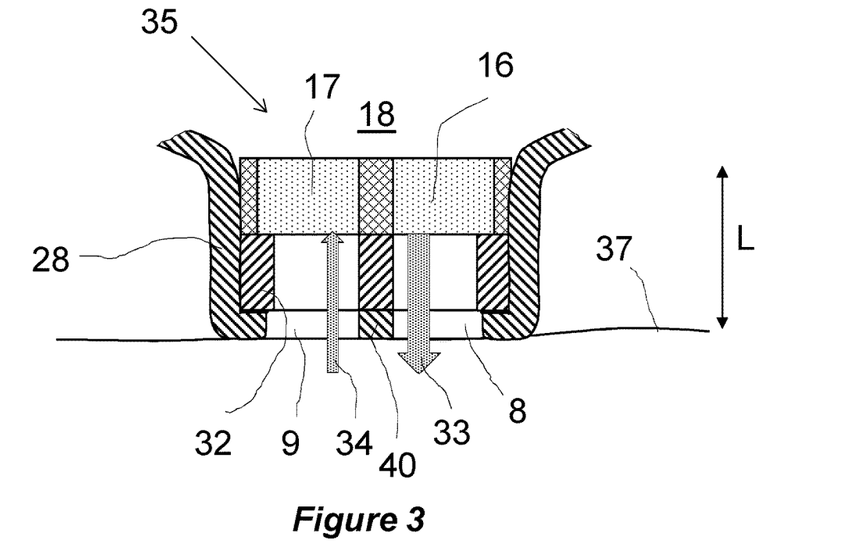
FIG. 3 is a cross-sectional schematic view through the earphone device at the area of a heart rate sensor.
Figure 4:
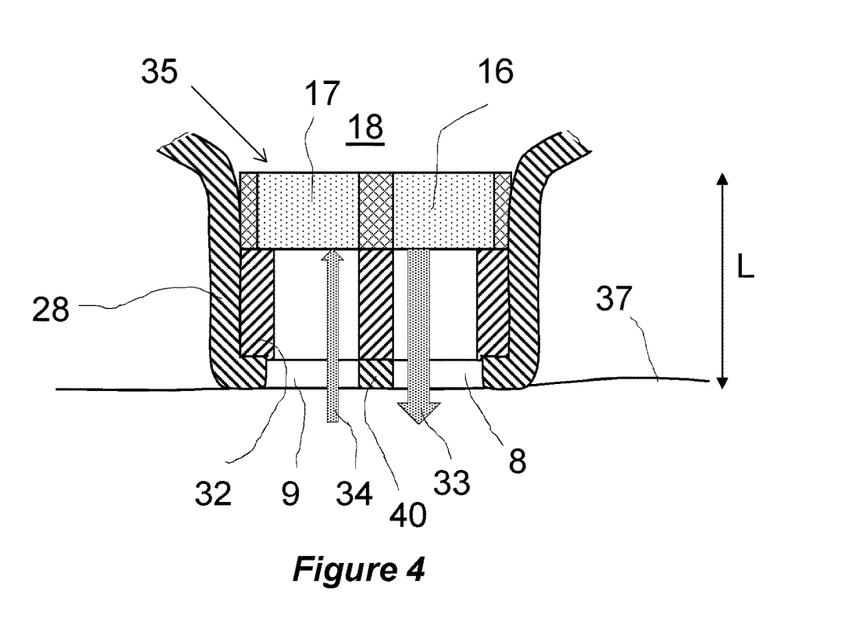
FIG. 4 is a cross-sectional schematic view corresponding to FIG. 3 with a fitting member with a longer sensor protrusion.

FIG. 3 is cross-sectional schematic view through the heart rate sensor 35 of the earphone device 1. The heart rate sensor 35 comprises a light emitter 16 and a light detector 17. The heart rate sensor 35 is protruding from the main body 18 and is received in the sensor protrusion 28 of the fitting member 4. The sensor protrusion 28 comprises a stiffening member 32 with two holes. The stiffening member 32 is made of hard plastic and prevents the sensor protrusion 28 from collapsing when it is pressed against the skin of the conchal wall 37. Light emitted 33 from the light emitter 16 is directed to the skin of the conchal wall 37. Some of the light is absorbed by the tissue and some 34 is scattered back to the light transceiver. As some of this received light 34 is affected by the pulsating blood in the blood vessels, the heart rate can be determined. The light detector transduce the backscattered light 34 into a signal, where only a small part of this signal represents the heart rate. Shakings due to the user's movements cause a lot of noise to the signal. However, a motion sensor in the earphone device 1 is used determine the noise signal to be subtracted in order to obtain a reliable heart rate signal. Under all circumstances, it is important to obtain a good and well-defined light sensing. Thus, it is important, that the end face 31 of the sensor protrusion 28 is abutting the skin of the conchal wall 37 so that no ambient light enters the second window 9 and disturbs the sensed signal. As the earphone device 1 comprises a speaker protrusion 26 to be arranged in the ear canal 15, it is necessary to be able to adjust the distance from the speaker protrusion 26 to the end face 31 of the sensor protrusion 28 to the user's ear in order to obtain a comfortable wearing. If the distance were fixed it would be necessary to choose a distance, which was long enough to ensure a "strong" enough abutment of the end face 31 against the skin for most users, which would cause discomfort for those with relatively small ears. According to this disclosure, the fitting member 4 with the sensor protrusion 28 can be replaced with another fitting member 4 with a sensor protrusion of another length L. Such a fitting member 4 is shown in FIG. 4.

Figures 5, 6:
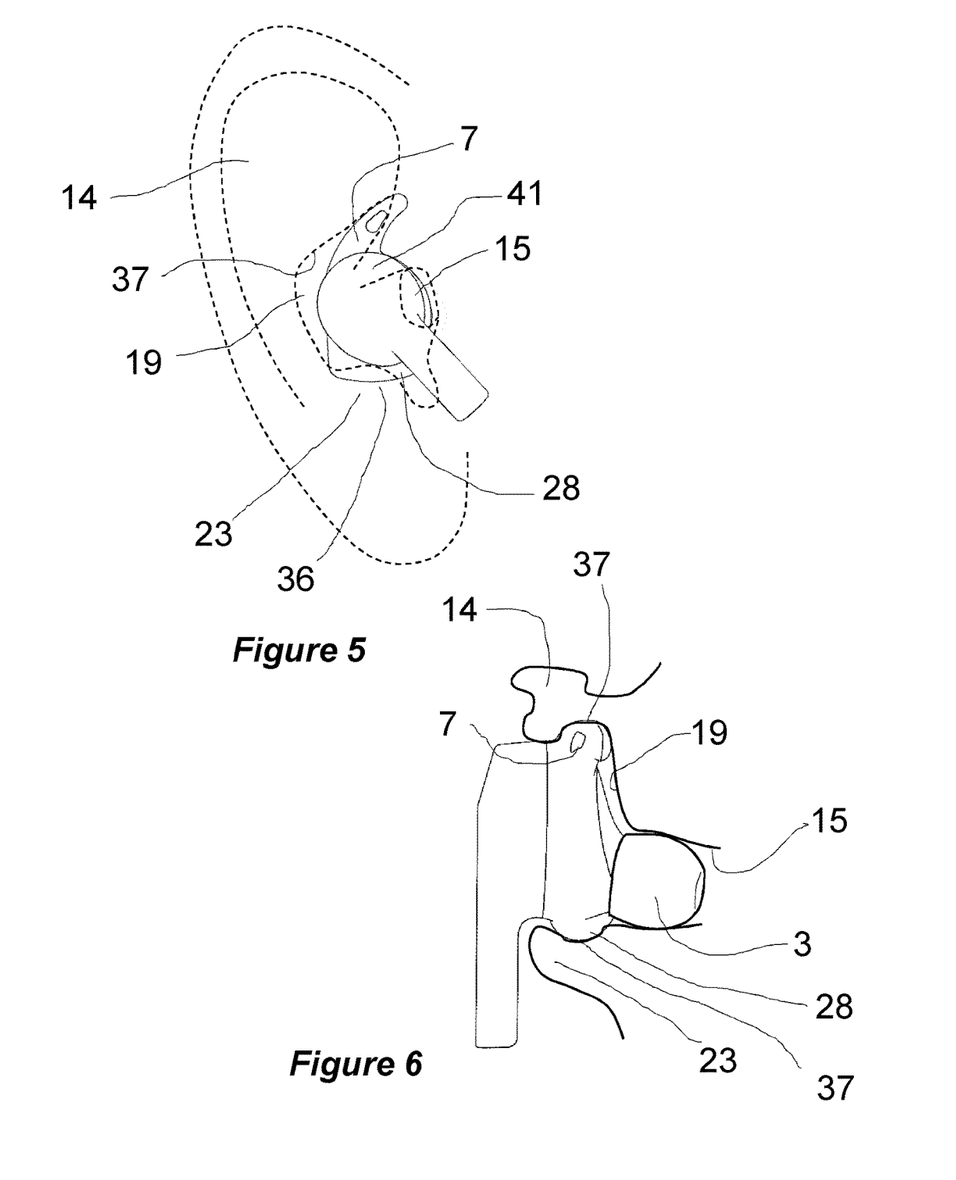
FIG. 5 is an earphone device according to the invention arranged in the ear of a user.
FIG. 6 is cross sectional view through the ear with the earphone device according to the invention.

In FIG. 5 the earphone device 1 arranged in the ear 14 of a user. The conchal wall stabilizer 7 is positioned at the crux of helix while the sensor protrusion 28 is abutting the conchal wall 37 at a sensing position 36 behind the antitragus 23.

FIG. 6 is a schematical cross sectional view through the ear 14 with the earphone device 1. The eargel 3 is positioned in the ear canal 15 and both the sensor protrusion 28 and the conchal wall stabilizer 7 abut the conchal wall, whereby a secure fitting of the earphone device 1 in the user's ear 14 is obtained.

Figure 7:
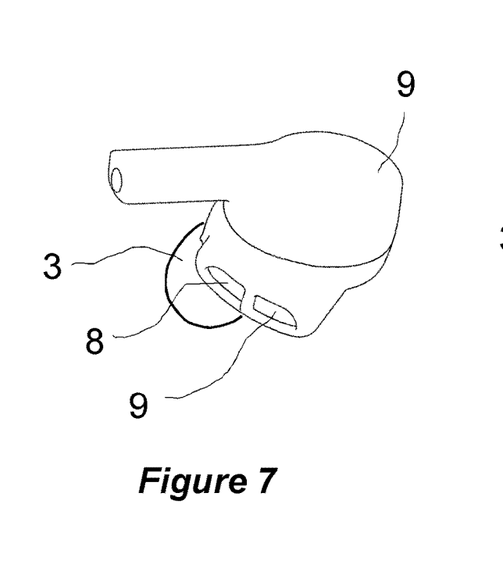
FIG. 7 is the earphone device seen from the outer side.
Figure 8:
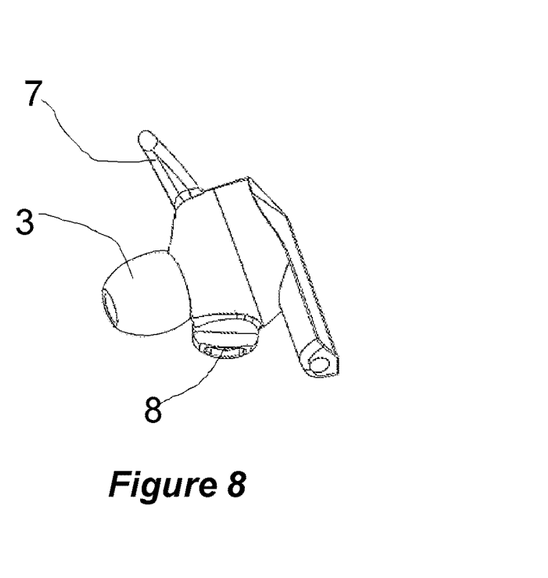
FIG. 8 is the earphone device seen from the side.

FIG. 7 is the earphone device 1 seen from the outer side, and FIG. 8 is the earphone device 1 seen from the side.

Figure 9:
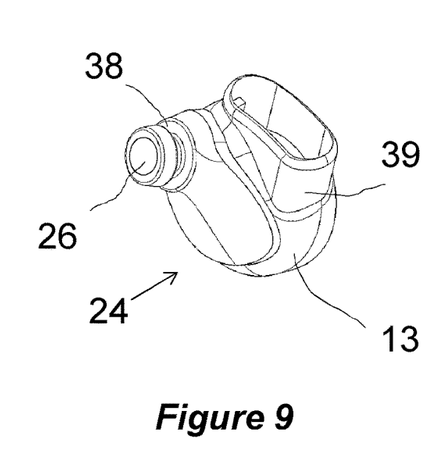
FIG. 9 is a first shell part of the main body of the earphone device.

FIG. 9 is a first shell part 24 of the main body 18 of the earphone device 1. The first shell part 24 is moulded in hard plastic. A sensor tower 39 is adapted to enclose the heart rate sensor 35. The speaker protrusion 26 comprises a retaining recession 38 by which the replaceable eargel 3 can be retained. The surface of the first shell part 24 comprises a recessed mounting area 13 which corresponds to the fitting member 4. When the fitting member 4 is mounted to the first shell part 24, the border of the mounting area fixates the fitting member 4.

Figure 10:
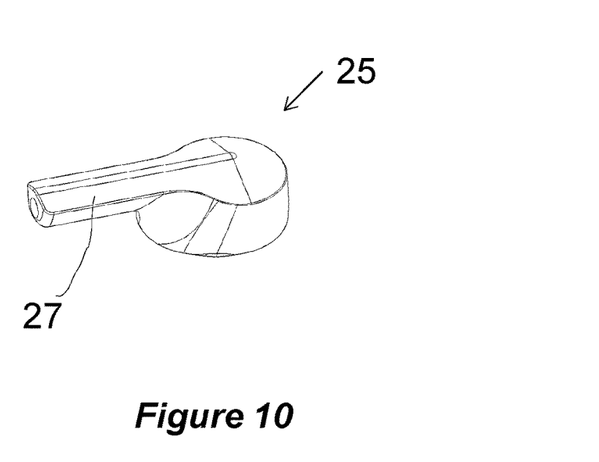
FIG. 10 is a second shell part of the main body of the earphone device.

FIG. 10 is a second shell part 25 of the main body 18 of the earphone device 1. The second shell part 25 is also moulded in hard plastic and forms the outer part of the main body 18. It comprises an elongated part 27, from which the cord 20 extends when the earphone device 1 is assembled.

Figure 11:
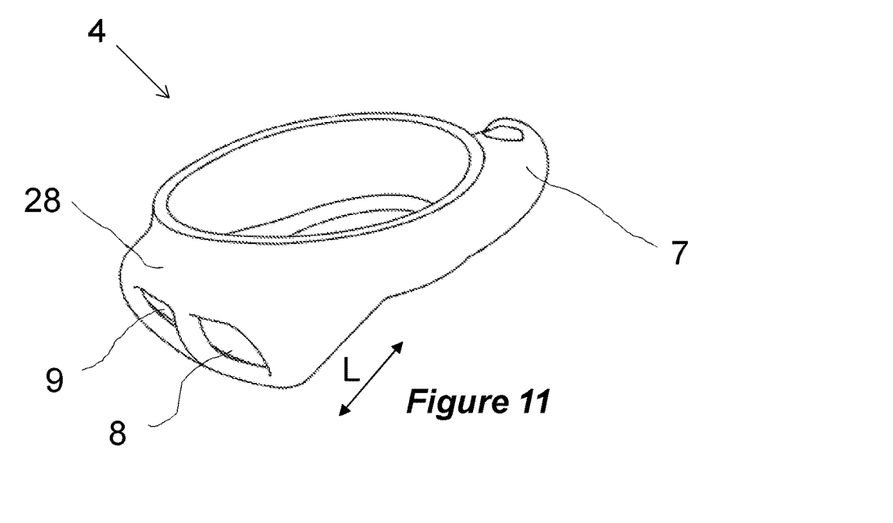
FIGS. 11, 12 and 13 are views of fitting members of different sizes.
Figures 12, 13:
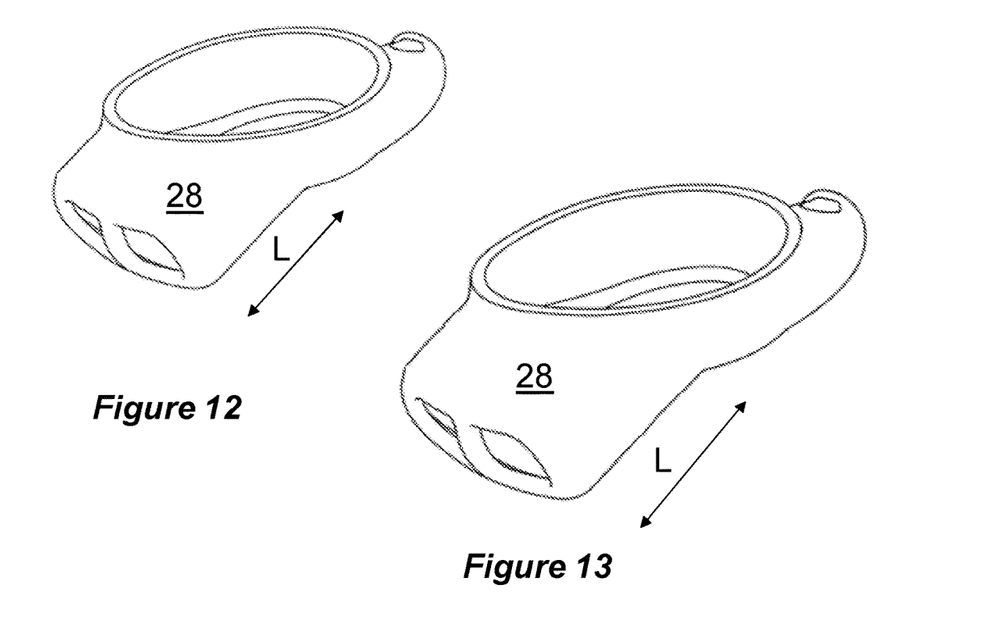

FIGS. 11, 12 and 13 disclose three fitting members 4 with sensor protrusions 28 of different lengths L. Thus, the user may mount the fitting member 4 with the best suited sensor protrusion length L for obtaining a reliable heart rate sensing and comfortable wearing. It is not shown here, but the size of the conchal wall stabilizer 7 may also vary.

The left earphone device 29 does not comprise an optical sensor 35. Instead, the protrusion corresponding to the sensor tower 39 comprises a micro-USB socket, which can be used for charging the rechargeable battery of the headset 1.

Figure 14:
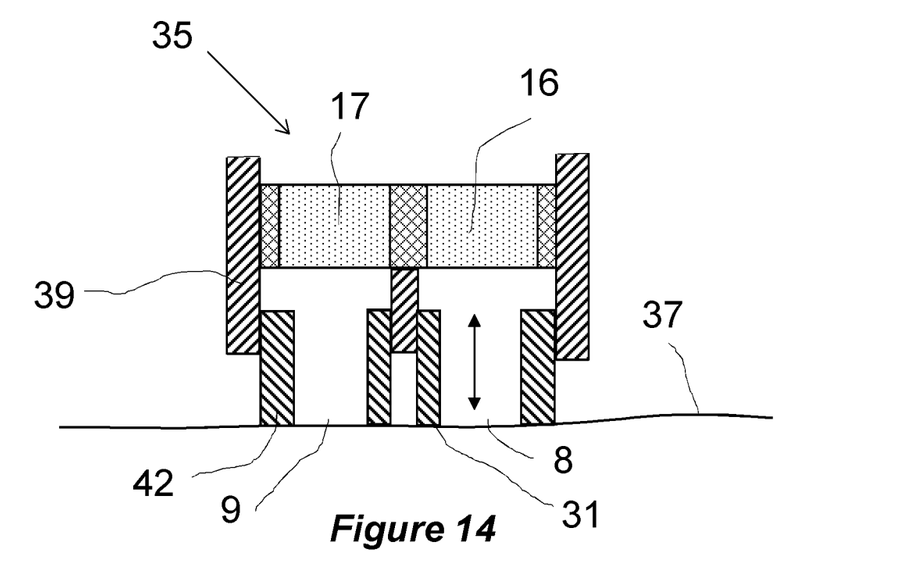
FIG. 14 is an earphone device according to a second embodiment.

FIG. 14 is an earphone device 44 according to a second embodiment. Here, a movable end face member 42 is arranged in front of the heart rate sensor 35. The distance between the speaker protrusion and the end face 31 can be adjusted by telescoping the end face member 42 along the arrow.

Figure 15:
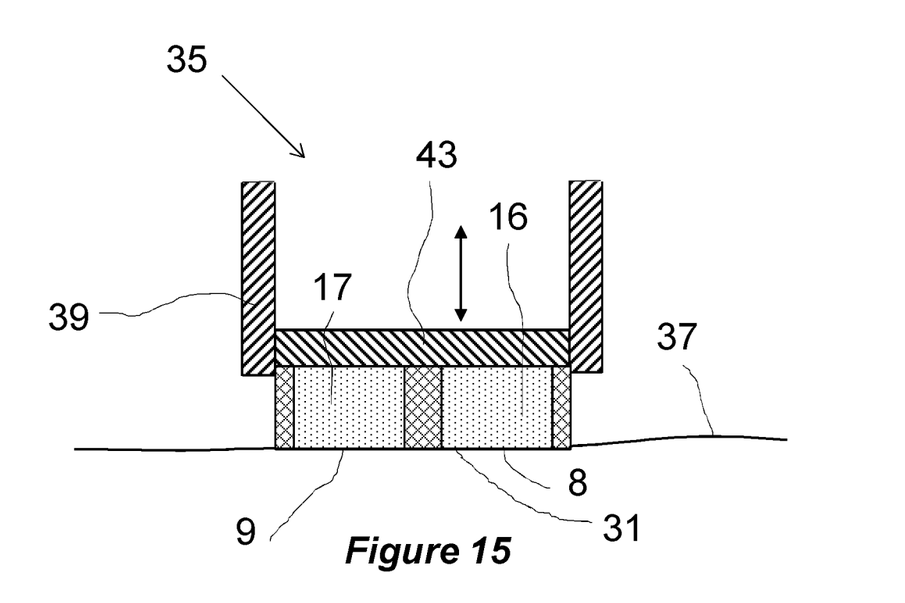
FIG. 15 is an earphone device according to a third embodiment.

FIG. 15 is an earphone device 45 according to a third embodiment. Here, the heart rate sensor 35 is arranged at the free end of a movable sensor member 43. The distance between the speaker protrusion and the end face 31 can be adjusted by displacing the sensor member 43 along the arrow.

| Reference signs: |
|---|
| 1 Earphone device |
| 2 Audio opening |
| 3 Eargel |
| 4 Resilient fitting member |
| 5 First side of earphone device |
| 6 Second side of earphone device |
| 7 Conchal wall stabilizer |
| 8 First window |
| 9 Second window |
| 10 Tip of conchal wall stabilizer |
| 11 Opening in fitting member |
| 12 Opening in conchal wall stabilizer |
| 13 Mounting area of main body |
| 14 Outer ear |
| 15 Ear canal |
| 16 light emitter |
| 17 light detector |
| 18 Main body |
| 19 Concha |
| 20 Cord |
| 21 Controller |
| 22 Strain relief |
| 23 Antitragus |
| 24 First shell part |
| 25 Second shell part |
| 26 Speaker protrusion |
| 27 Elongated part of second shell part |
| 28 Sensor protrusion of fitting member |
| 29 Second earphone device |
| 30 Headset |

| -continued |
|---|
| Reference signs: |
| 31 End face of sensor protrusion |
| 32 Stiffening member |
| 33 Emitted light |
| 34 Received light |
| 35 Heart rate sensor |
| 36 Sensing position |
| 37 Conchal wall |
| 38 Retaining recession |
| 39 Sensor tower |
| 40 Wall |
| 41 Crux of helix |
| 42 Adjustable end face member |
| 43 Adjustable sensor member |
| 44 Earphone device |
| 45 Earphone device |
| L length of sensor protrusion of fitting member |

The invention claimed is:

1. An earphone device to be worn in the ear, comprising: a main body to be placed in the concha of the outer ear of a user and a movable sensor, which includes an emitter and a detector capable of transmitting a signal between said emitter and detector, and a window through which the signal can be transmitted,
the window including an end face abutting a conchal wall at a sensing position,
wherein the earphone device is positioned in the outer ear, so that the end face is abutting the conchal wall in the lower end of the concha adjacent the antitragus, and
wherein the end face is adjustable so that the main body, which includes a speaker protrusion, can be inserted into an ear canal, and that the distance between the speaker protrusion and the sensor position is adjustable to bring the sensor in closer proximity with the user's ear.

2. An earphone device according to claim 1, wherein the earphone device furthermore comprises a fitting member detachably attached to the outer side of the main body, and wherein the fitting member includes the window.

3. An earphone device according to claim 1, wherein the distance between the speaker protrusion and the end face is adjustable.

4. An earphone device according to claim 2, wherein the end face is provided at the end of a protruding sensor protrusion with a certain length.

5. An earphone device according to claim 2, wherein the fitting member comprises a first window for transmitting light emitted from the light emitter to the skin of the ear and a second window for transmitting light from the skin of the ear to the light detector.

6. An earphone device according to claim 5, wherein the first window and second window are divided by a wall of material, which is non-transparent for the light emitted by the light emitter.

7. An earphone device according to claim 2, wherein the fitting member comprises a protruding conchal wall stabilizer which engages the conchal wall at a second position at the crus of helix.

8. A headphone comprising an earphone device according to claim 2 comprising a plurality of replaceable fitting members of different sizes, whereby the distance between the speaker protrusion and the end face can be adjusted by replacing one of the fitting members with another fitting member.

9. An earphone device according to claim 1, wherein the end face is provided at the end of an adjustable telescopic end face member.

10. An earphone device according to claim 1, comprising a resilient earbud detachably attached to the speaker protrusion.

11. An earphone device according to claim 1, wherein the main body and the speaker protrusion are embodied as a unitary non-resilient body.

* * * * *